United States Patent
Nakamura et al.

(10) Patent No.: US 7,234,290 B2
(45) Date of Patent: Jun. 26, 2007

(54) PROCESS FOR PRODUCING ASPHERIC SEAMLESS CAPSULE AND APPARATUS THEREFOR

(75) Inventors: Takeshi Nakamura, Tokyo (JP); Toshinari Taira, Tokyo (JP); Kenta Wada, Tokyo (JP); Katsuya Otomo, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 45 days.

(21) Appl. No.: 10/519,087

(22) PCT Filed: Jun. 20, 2003

(86) PCT No.: PCT/JP03/07885

§ 371 (c)(1),
(2), (4) Date: Sep. 20, 2005

(87) PCT Pub. No.: WO04/000201

PCT Pub. Date: Dec. 31, 2003

(65) Prior Publication Data

US 2006/0096252 A1 May 11, 2006

(30) Foreign Application Priority Data

Jun. 24, 2002 (JP) .............................. 2002-183447

(51) Int. Cl.
*B65B 47/02* (2006.01)
*B01J 13/20* (2006.01)
*A61J 3/07* (2006.01)

(52) U.S. Cl. ............................ 53/454; 53/560; 53/900; 424/451; 264/4.6; 425/5

(58) Field of Classification Search .................. 53/428, 53/440, 454, 113, 122, 127, 560, 900; 264/4, 264/4.6; 424/451; 425/5
See application file for complete search history.

(56) References Cited

FOREIGN PATENT DOCUMENTS

EP 90600 A2 10/1983

(Continued)

OTHER PUBLICATIONS

Machine generated English language translation of JP 2000-325431.*

*Primary Examiner*—Stephen F. Gerrity
(74) *Attorney, Agent, or Firm*—Morgan, Lewis & Bockius LLP

(57) ABSTRACT

In manufacturing an aspherical seamless capsule comprises, firstly, a seamless capsule C1 having a filler encapsulated with a shell membrane is provided, then it is dried in a dryer 12 until a predetermined percentage content of solvent in the shell membrane reaches a predetermined value. Subsequently, the seamless capsule is heated by a heater 38 so that the shell material may get to a semi-sol state. Then, the heated seamless capsule is formed into an aspherical shape using a forming machine such as a compression molding machine. Because the spherical seamless capsule has a shell membrane which is dried to get semi-sol so that it may have a reduced elasticity and a shortened stress relaxation time, the capsule can be formed in a short time and suppressed from restoring to the original spherical shape. The semi-sol shell membrane has almost no change in properties, and so allows easiness in temperature control for treatment. The aspherical capsule after being formed does not or rarely need drying, resulting in wrinkle resistance and little variation in shape brought on the surface of the shell membrane.

6 Claims, 6 Drawing Sheets

FOREIGN PATENT DOCUMENTS

| | | | |
|---|---|---|---|
| GB | 2088273 | * | 6/1982 |
| JP | 52-79019 A | * | 7/1977 |
| JP | 60-40055 A | * | 3/1985 ................... 264/4 |
| JP | A-2000-325431 | | 11/2000 |
| WO | WO 92/21311 A1 | | 12/1992 |
| WO | WO 01/45635 A1 | | 12/2000 |
| WO | WO 01/68032 A1 | | 9/2001 |

* cited by examiner

PROCESS FOR PRODUCING ASPHERIC SEAMLESS CAPSULE AND APPARATUS THEREFOR

TECHNICAL FIELD

The present invention relates to a method and an apparatus for manufacturing a seamless capsule, especially an aspherical seamless capsule, formed by encapsulating a filler of a medicine, a flavor, a spice, a perfume or the like with a capsule shell material of gelatin or the like.

BACKGROUND ART

As a method for manufacturing a so-called seamless capsule, there has been known a method wherein a liquid filler is flown out of the central nozzle of a multiple nozzle, a liquid capsule shell material is simultaneously flown out of an annular nozzle surrounding the central nozzle, and they are cut to drop into a cooling liquid (curing liquid). In this method, a droplet is dropped in the cooling liquid to change into a spherical shape, and then the shell material is gelled to stabilize the spherical shape.

A seamless capsule having an aspherical shape such as an elliptic shape, an oval shape, and a both side evenly convex spherical shape as seen in a popular capsule is desired from the viewpoints of easy taking, simple treating or product differentiation.

Conventionally, some methods have been proposed. For example, the methods are a method in which the spherical seamless capsule obtained by the above method is reformed into an aspherical shape through a proper forming device before drying the capsule, and a method in which the spherical seamless capsule is heated to convert its capsule shell membrane from a gel state to a sol sate before drying, and is formed into an aspherical shape through a proper forming device, and the aspherical seamless capsule thus obtained is then cooled to gel the shell membrane to stabilize the shape followed by drying, as described in JP Application Laid-Open No. 2000-325431.

However, the conventional methods for manufacturing an aspherical seamless capsule mentioned above have problems as follows.

In the former method, the spherical seamless capsule, whose shell membrane has a high percentage of water content and so is highly elastic before drying, is likely to return into its original spherical shape. Also, this method has a problem that it takes a long time to form into the aspherical shape because of a long stress relaxation time.

The latter method, described in JP Application Laid-Open No. 2000-325431, takes a relatively short time to form into an aspherical shape. However, the gelled spherical seamless capsule, which has a high percentage of water content before drying, is heated to convert to the sol with remarkable changes in physical properties caused by a sol/gel transformation. Therefore, the method has a problem that the seamless capsule is difficult to treat and requires a strict temperature control. Both of the methods described above also have a problem that the seamless capsule formed into an aspherical shape is dried to cause the shell membrane to shrink, resulting in wrinkles on the membrane surface and variation in shape.

The object of the present invention is to provide a method and an apparatus for manufacturing an aspherical seamless capsule to solve the problems described above.

DISCLOSURE OF THE INVENTION

In order to achieve the object described above, a method for manufacturing an aspherical seamless capsule of the present invention comprising the steps: a first step for providing a seamless capsule having a filler encapsulated with a shell membrane; a second step for drying the seamless capsule provided in the first step until a predetermined percentage content of solvent in the shell membrane reaches a predetermined value; a third step for heating the seamless capsule obtained in the second step so that the shell material may get to a semi-sol state; and a fourth step for forming the seamless capsule obtained in the third step into a predetermined aspherical shape.

The term "semi-sol state" described herein is referred to as a state within a range that a gel structure is heated to change from the partial destruction to the complete sol. Additionally, the term means a state in which the membrane is not yet destructed to cause a filler to flow out even if loaded with an external force such as a compression.

As described above, according to the present invention, the seamless capsule, which uses the semi-sol shell membrane after drying, i.e. a membrane having a reduced elasticity and a short stress relaxation time, can be formed in a short time and does not return back to the original spherical shape. Also, few changes occur in the physical properties of the semi-sol membrane, resulting in easy control of temperature in the forming. The seamless capsule thus formed into the aspherical shape is unnecessary or little necessary to dry, resulting in no wrinkles on the shell membrane surface and little variation in shape.

The shell membrane of the seamless capsule is dried to a degree for providing the effect described above. A membrane, if it comprises a material using water as a solvent such as an aqueous gelatin solution, is preferably dried in the second step to have a percentage of solvent content (water content) of 20% by weight or less.

A process using microwave is preferable for a heating process in the third step, though many other processes are available.

For forming in the fourth step, a compression molding process using dies is simple and reliable. An apparatus to carry out the compression molding process includes an apparatus having two dies facing each other and an apparatus having a die and a punch. They can be preferably used.

In order to stabilize rapidly a seamless capsule in shape, it is effectively cooled simultaneously while being forming.

In regard to the relation between the heating in the third step and the forming in the fourth step, the capsule may be formed not only after heated, but also while heated.

An apparatus for manufacturing an aspherical seamless capsule according to the present invention comprises: a heating part for heating a spherical seamless capsule having a filler encapsulated with a shell membrane; and a forming part for forming the seamless capsule into an aspherical shape, while the shell membrane of the seamless capsule heated by the heating part is in a semi-sol state. For the forming part, a compression molding machine having a die or punch described above may be used. For the heating part, a heater using microwave is preferable.

A seamless capsule, which is dried to have a predetermined percentage of solvent content, can be applied to the heating part of the apparatus to carry out preferably a method of the present invention described above.

BEST MODE FOR CARRYING OUT THE INVENTION

Figure 1:
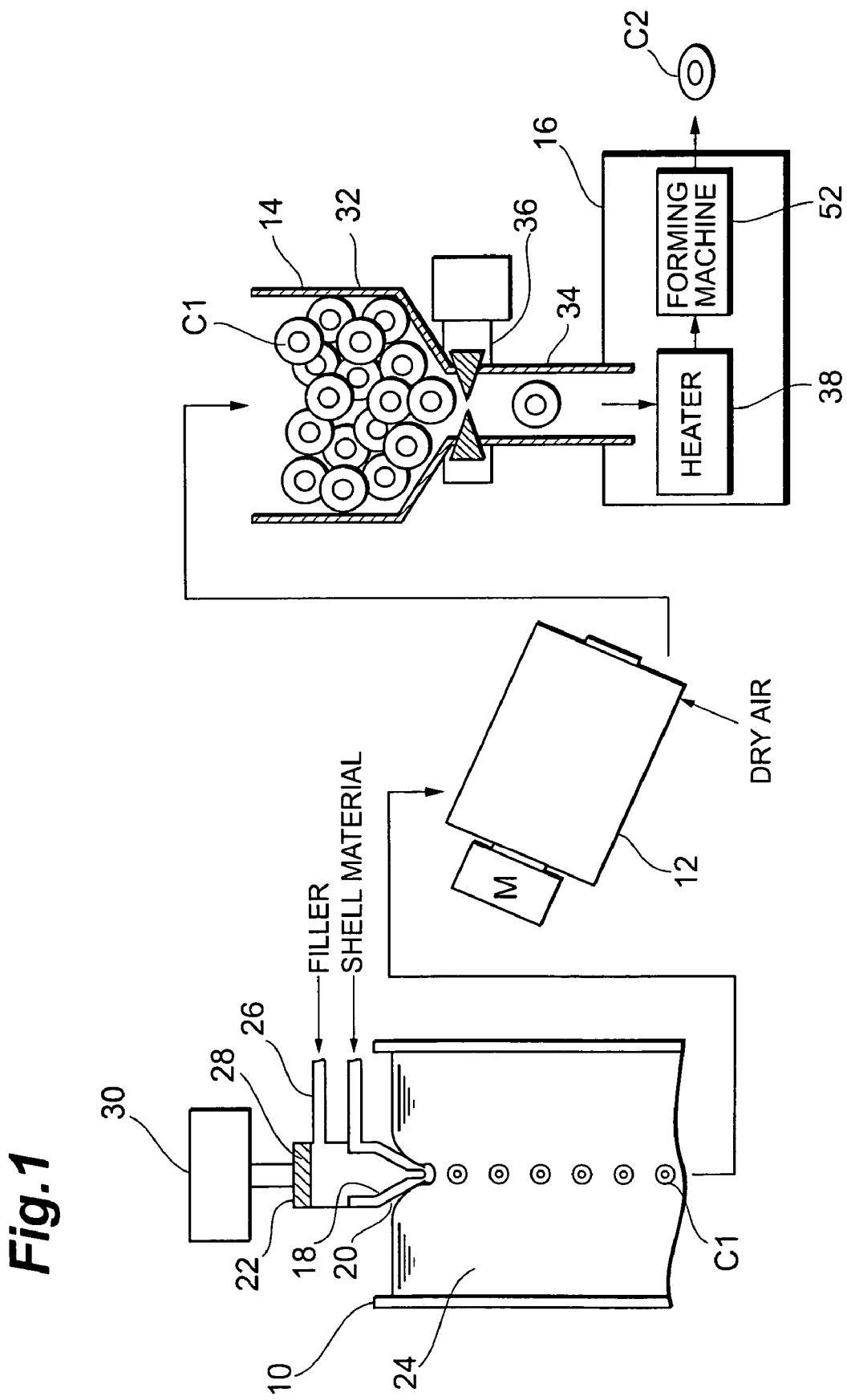
FIG. 1 schematically shows a construction of an apparatus for use in manufacturing an aspherical seamless capsule according to the present invention.

Now, referring to the drawings, preferable embodiments of the present invention will be explained in detail.

FIG. 1 schematically shows the whole construction of an apparatus for manufacturing an aspherical seamless capsule (hereinafter, seamless capsule is called only "capsule") according to a method of the present invention. In FIG. 1, the numeral 10 shows a machine for manufacturing a spherical capsule C1, the numeral 12 shows a dryer for drying the spherical capsule C1 prepared by the spherical capsule manufacturing machine 10, the numeral 14 shows a storage for temporally storing the spherical capsule C1 dried by the dryer 12, and the numeral 16 shows an aspherical capsule manufacturing apparatus for manufacturing an aspherical capsule C2 from the spherical capsule C1.

A known spherical capsule manufacturing machine 10 is available, for example, a machine disclosed in International Publication No. WO01/45635A1. The spherical capsule manufacturing machine 10 described in the International Publication comprises a multiple nozzle 22 including a central nozzle 18 opening downward and an outer nozzle 20 coaxially surrounding the central nozzle 18. The central nozzle 18 is supplied with a liquid filler which will be filled inside a spherical capsule C1, and a circular space between the central nozzle 18 and the outer nozzle 20 is supplied with a sol-state capsule shell material which will become a capsule shell membrane of the spherical capsule C1.

Here, the shell material is not limited to a specific kind, as long as it has a property to allow reversible sol/gel transformation even after dried. A material having the said property includes, for example, gelatin, agar, starch, carrageenan, alginic acid, or a gum such as guar gum and xanthan gum. A material containing gelatin and a plasticizer is preferable for the shell material of the seamless capsule. If necessary, the shell material may contain an additive such as a light blocking agent.

For the gelatin, a gelatin derived from an animal such as a cow or pig is available. The gelatin which has a property to allow the reversible sol/gel transformation, includes an alkali treated gelatin, an acid treated gelatin, and a chemically modified gelatin. These gelatins may be used alone or in a combination.

The plasticizer includes, for example, glycerin, sorbitol, maltose, glucose, maltitose, sucrose, xyltol, mannitol, propylene glycol, or polyethylene glycol. The light blocking agent includes caramel, titanium oxide, or iron oxide.

Although the filler may be obtained by dissolving a drug such as pharmaceutical, flavor, spice or fragrance, for example, in a solvent including a medium chain triglyceride, an animal or vegetable oil such as soybean oil, olive oil and lard, liquid paraffin or mineral oil, any suitable material may be used as the filler, as long as it is a liquid material that does not dissolve the shell material of a seamless capsule. The filler may contain an additive such as an auxiliary solubilizer or a stabilizer for the drug. The auxiliary solubilizer includes an alcohol such as ethanol.

The lower ends of the central nozzle 18 and the outer nozzle 20 of the multiple nozzle 22 are immersed in a curing liquid (cooling solution) 24, or positioned downward above the surface of the curing liquid 24. The curing liquid 24 can convert the shell material to the gel by touching the shell material. The curing liquid 24 may be selected from a liquid paraffin, a medium chain triglyceride or the like, if the shell material contains gelatin.

The inner space of the multiple nozzle 22, into which the filler is introduced through a tube 26, is provided with a movable wall 28 at the upper portion thereof. The movable wall is constituted by a flexible film which defines a part of the wall of the inner space. The movable wall 28 is moved up and down by a vibrator 30, and can send a vibration having a given frequency and amplitude to the filler in the inner space of the nozzle. As a result, the motion of the movable wall 28 creates a pulse wave that is transmitted downward within the filler.

In the spherical capsule manufacturing machine 10 having the construction described above, the multiple nozzle 22 is supplied with the filler to flow it out of the central nozzle 18 downward, and is simultaneously supplied with the shell material to flow it out of the outer nozzle 20 downward in such a way that the shell material may surround the flow of the filler. Then, the movable wall 28 is moved up and down at a proper timing to cause a pulse wave within the filler, so that the filler from the center nozzle 18 is cut. At the same time, the vibration is transferred to the shell material, so that the shell material from the outer nozzle 20. Thus, droplets, in each of which the filler is coated with the shell material, are formed successively. The droplet gradually becomes spherical due to its surface tension while it is falling down in the curing liquid. The shell material in the surface of the droplet is contacted with the curing liquid 24 to be cooled or reacted, so that it gradually gets gelled (cured) to provide the spherical capsule C1.

The dryer 12 dries the spherical capsules C1 obtained by the spherical capsule manufacturing machine 10, and may be a continuous type or a batch type. For the batch type, a known rotary drum type dryer 12 can be used.

The storage 14 stores the dried seamless capsules C1 which are taken out from the dryer 12. The storage 14 is not necessarily required. It is also possible to transfer directly the spherical capsules C1 from the dryer 12 to an aspherical seamless capsule manufacturing apparatus 16. However, the seamless capsules C1 are effectively stored in the storage 14 until the manufacture of the aspherical seamless capsules C2 are started because the dried seamless capsules C1 are storable for a long time to allow more free planning of production. The storage 14 in this embodiment is provided with a receptacle 32 for holding the spherical capsules C1 and a fall chute 34 that is placed at the bottom of the receptacle 32. The fall chute 34 is provided with a distributor 36, which can open and close a capsule transfer route to fall the spherical capsule C1 one by one.

Figure 2:
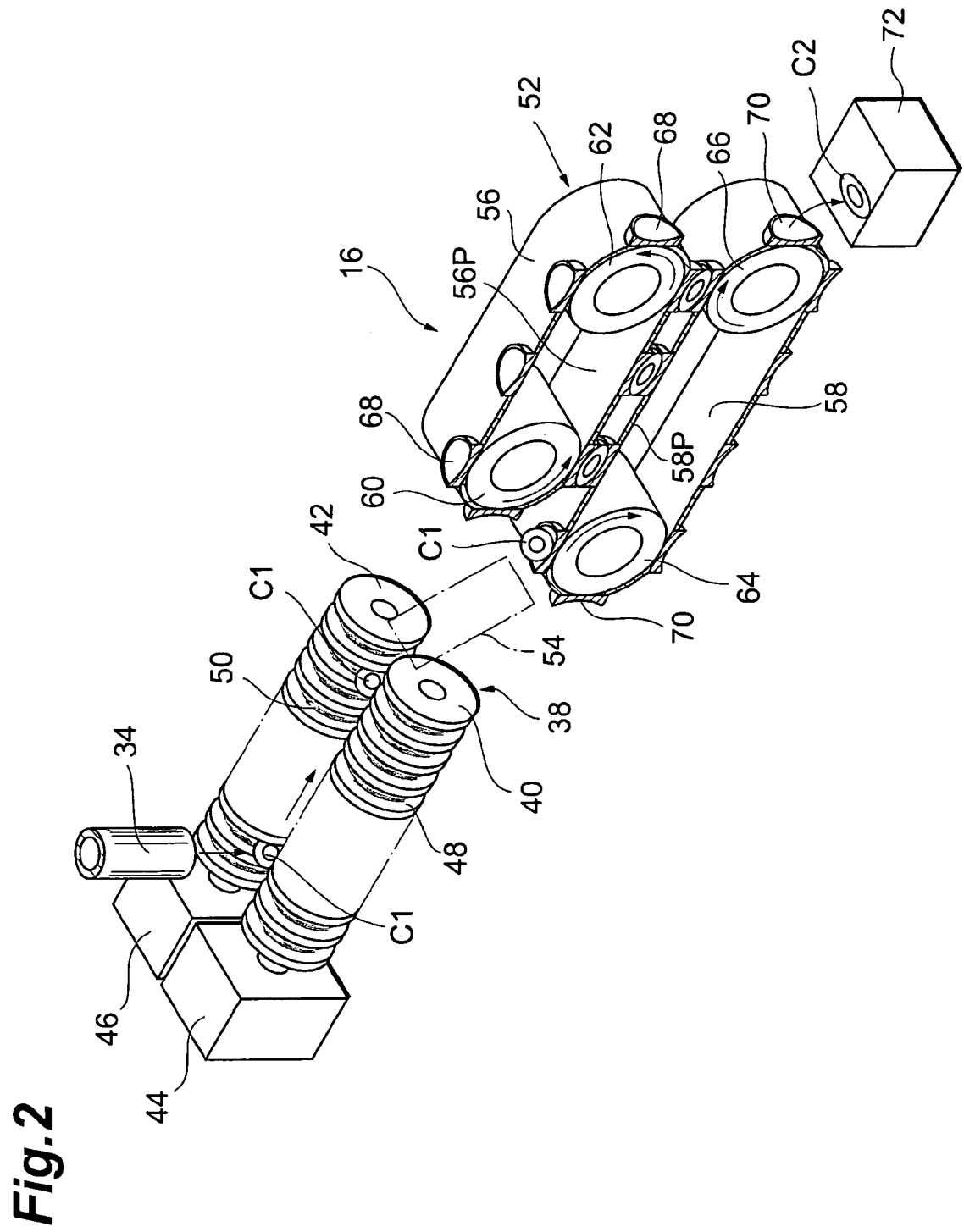
FIG. 2 shows one embodiment of an apparatus for manufacturing an aspherical seamless capsule of the present invention.

FIG. 2 shows a preferable embodiment of an aspherical capsule manufacturing apparatus 16 in accordance with the present invention. In FIG. 2, the numeral 38 shows a heater (heating part) to heat the spherical capsule C1. The heater 38 has a transferring function and uses a mechanism known as a biaxial roller conveyer. In other words, the heater 38 comprises rollers 40 and 42 which are disposed adjacent each other and in parallel to each other, and driver 44 and 46 for rotating the rollers 40 and 42 in the same rotation direction. Spiral grooves 48 and 50 having the same pitch are formed on the outer surfaces of the rollers 40 and 42, respectively. A peak between adjacent grooves 48, 48 of one roller 40 is positioned to face just against a peak between adjacent grooves 50, 50 of another roller 42. The spherical capsule C1 is put in a concave portion between the rollers 40 and 42 of the biaxial heater 38, and then the rollers 40 and 42 are rotated by drivers 44 and 46, resulting in the spherical capsule C1 being transported from one end to another while tumbling in the grooves 48 and 50 of the rollers 40 and 42. The heater 38 is not limited to the biaxial roller type.

The storage 14 is disposed above the said one end of the heater 38, and a lower opening end of the fall chute 34 of the storage 14 is positioned vertically above the concave portion between the rollers 40 and 42. At another end of the concave portion between the rollers 40 and 42, there is disposed a loader 54. The loader 54 can receive the spherical capsule C1 transferred to the end of the rollers, and transfer and load it to a forming machine (forming part 52). For the loader, a device that can control the opening/closing of a transferring route is available.

Inside the rollers 40 and 42 of the heater 38, their respective routes are provided to allow a liquid heat medium to flow therethrough, though they are not shown in the figures. The routes are connected to the other routes that pass through a heat source such as an electric heater placed outside the rollers 40 and 42. A pump is driven to circulate the heat medium through the routes, so that the surfaces of the rollers 40 and 42 are heated to a desired temperature. Of course, various means for heating a capsule, for example, a heating means for contacting with a heat source such as an electric heater or a high frequency heater, can be used. Not only a means for contacting with a heater to transfer the heat to the spherical capsule C1, but also a means for transmitting ultrasonic wave to the spherical capsule C1 to heat, a means for blowing high temperature air to the spherical capsule C1, and a means for irradiating microwave or infrared ray to the spherical capsule C1 are available.

In the shown embodiment, a compression molding type machine is used as the forming machine 52, and it comprises endless belts 56 and 58 which are arranged vertically. The upper and lower belts 56 and 58 are wrapped between pairs of pulleys 60 and 62; 64 and 66, respectively, and driven to circulate toward directions shown by arrows in the FIG. 2. The lower running part 56P of the upper belt 56 is placed above the upper running part 58P of the lower belt 58 with a given space between them. On the surfaces of the belts 56 and 58, a plurality of dies 68 and 70 as a forming jig are fixed at a given interval along the circulating direction of the belts 56 and 58. An upside die 68 and a corresponding downside die 70 are mutually assembled to form a space between their facing surfaces. The space has a shape which is almost the same to that in outline of an aspherical seamless capsule C2 to be manufactured. These upside and downside dies 68 and 70 are aligned to make pairs, when they are positioned in the lower running part 56P and the upper running part 58P of the endless belts 56 and 58, respectively.

The distance between pulleys 60 and 62 of the upper belt 56 is shorter than that of the lower belt 58. Thus, the upper running part 58P of the lower belt 58 has an upward exposed terminal area on the side of the driven pulley 64, above which the outlet of the loader 54 is located.

Now, a method for manufacturing the aspherical capsule C2 by use of the apparatuses described above will be explained.

First, as mentioned above, the filler and the capsule shell material are supplied to the multiple nozzle 22 in the spherical capsule manufacturing machine 10, and droplets having the filler encapsulated the shell material are immersed in the curing liquid 24, thereby manufacturing spherical capsules C1. In this embodiment, the shell material of the spherical capsule C1 is made of gelatin, glycerin and purified water, and the filler of the spherical capsule C1 consists of medium chain triglyceride in which a medicine such as a flavor is dissolved by using absolute ethanol as an auxiliary solubilizer.

Next, after the spherical capsules C1 prepared by the spherical capsule manufacturing machine 10 are taken out of the curing liquid 24, they are transferred to the dryer 12 and dried until their shell membranes have a predetermined percentage of solvent content. In the present embodiment, the solvent for the shell material is water, and so the percentage of solvent content means a percentage of water content. The percentage of water content in the shell membrane of the spherical capsule C1 dried by the drier 12 is the one in which after forming the spherical capsule C1 into an aspherical capsule, the force for restoring the aspherical capsule to the original spherical capsule is reduced to a desired degree. Specifically, the percentage of water content in the shell membrane is preferably 20% by weight or less, more preferably 15% by weight or less, and particularly preferably 10% by weight or less.

The percentage is particularly preferably 10% by weight or less, because, as described later, the aspherical capsules C2 manufactured by using the well dried spherical capsules C1 can be easily stored or handled during transporting, and because the aspherical capsules C2 after taken out of the aspherical capsule manufacturing apparatus 16 need no further drying.

The percentage of water content in the shell membrane can be determined from a lost weight after a spherical capsule C1 is placed at a high temperature (i.e., 105° C.) for a given time (i.e., 2 hours) in a measurement chamber (method of loss on drying).

The spherical capsules C1 taken out of the dryer 12 are stored in the storage 14. Since the spherical capsules C1 are dried to cure the shell membranes sufficiently, they do not adhere to each other and easily managed in the storage 14, resulting in a long term storage. Also, since the capsules are easily handled, no problem may occur even if the storage 14 or the aspherical capsule manufacturing apparatus 16 is apart from the dryer 12 by a long distance.

In order to manufacture the aspherical capsules C2 from the dried spherical capsules C1, the aspherical capsule manufacturing apparatus 16 is started up. Then, the rollers 40 and 42 of the heater 38 start rolling and, at the same time, a liquid heat medium heated to a high temperature by a heating source flows through the routes within the rollers 40 and 42, resulting in heating the surface of the rollers 40 and 42 to a predetermined temperature. The belts 56 and 58 of the forming machine 52 are also driven.

In this stage, the dried spherical capsules C1 are transferred one by one to the space between the rollers 40 and 42 of the heater 38 from the storage 14. The spherical capsules C1 that are transferred to the space between the rollers 40 and 42 move to the direction of the feeder 54 while being heated. Each spherical capsule C1 is tumbled within the grooves 58 and 50 of the rollers 40 and 42 to heat the whole surface of the capsule evenly. When the spherical capsule C1 reaches the end of the heater 38, the temperature of the whole surface of the shell membrane reaches a given value and the membrane becomes semi-sol state.

The term "semi-sol state" described herein is referred to as a state within a range from a partial destruction of a gel structure due to heating to the sol-state. Additionally, the term "semi-sol state" means a state in which the membrane is not yet destructed to cause a filler to flow out even if loaded with an external force such as a compression imposed by the forming machine 52.

Figure 3:
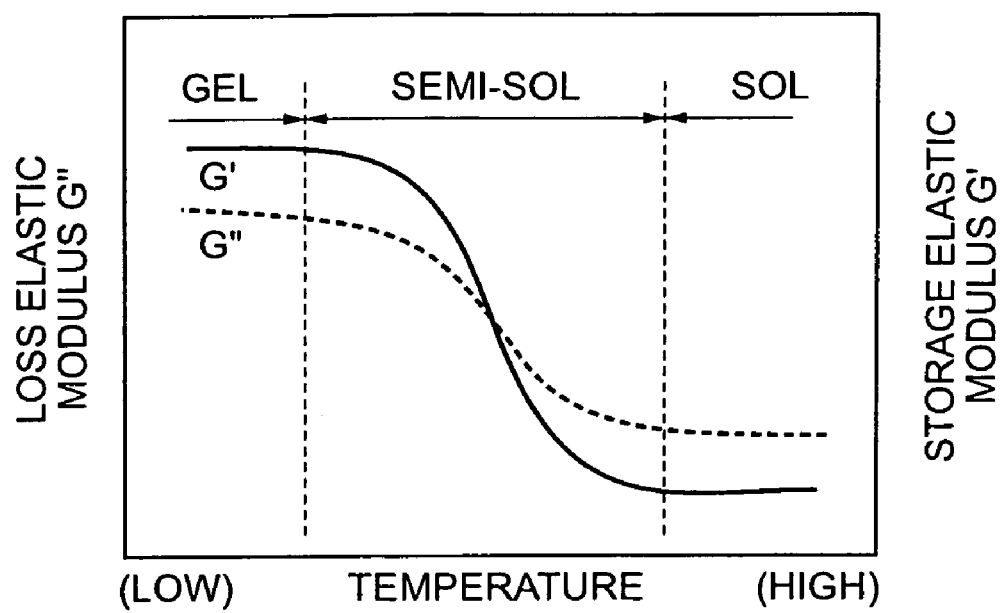
FIG. 3 is a graph showing schematically the relation between a temperature and a storage elastic modulus or a loss elastic modulus of a shell membrane.

The time point in which the partial destruction of the gel structure begins and the time point in which the structure reaches the sol state can be determined from responses (storage elastic modulus (G') and loss elastic modulus (G'')) observed when a test substance (a test film having a membrane thickness of about 1 mm) is heated/cooled with vibration loaded to deform by using a viscoelasticity measurement device (Rheometer available from TA Instruments). A relation between temperature and storage elastic modulus (G'), and a relation between temperature and loss elastic modulus (G'') are as shown in FIG. 3. The term "semi-sol state" described herein indicates a state within a range wherein a storage elastic modulus (G') and a loss elastic modulus (G'') start at their respective plateau levels to fall down to their respective another plateau levels with respect to temperature. For example, in this embodiment, when a surface temperature of a shell membrane, which contains gelatin and glycerin and has a water content of 10% by weight, reaches about 80 to 120° C., the membrane becomes a semi-sol state. A temperature at which the G'' and G' become equal (their lines are crossing in the graph) is expediently called a sol-gel transition point.

It should be noted that, in order to suppress a capsule from returning back to the original shape after it is formed by the forming machine 52, its shell membrane has preferably a higher surface temperature than a temperature at which the membrane starts shifting from the gel to the semi-sol. Further, in order to prevent the shell membrane from being broken, the membrane has preferably a lower surface temperature than a temperature at which the membrane reaches complete sol state. Therefore, a shell membrane, which contains gelatin and glycerin and has a water content of 10% by weight, is preferably heated to have a surface temperature of 90 to 110° C., and more preferably 95 to 110° C. The shell membrane having a low percentage of water content, may be heated at a relatively wider range of temperature, and so it is easy to control the temperature.

Each of the spherical capsules C1, whose shell membrane is heated by the heater 38 to get a semi-sol state, is transferred through the loader 54 to the forming machine 52 at a proper timing, and set in the concave of the lower die 70 positioned on the exposed area of the lower belt 58P. The lower die 70 is moved with circulation of the belts 56 and 58, and aligned with the corresponding upper die 68 of the lower running part 56P of the upper belt 56. The spherical capsule C1 is compressed between the dies 68 and 70. The capsule that is compressed between the dies 68 and 70, while kept to be compressed, is fed to another ends of the upper and lower belts 56 and 58 (the end point of driving pulley 62 and 66), and then the upper and lower dies 68 and 70 are separate from each other.

Since the upper and lower dies 68 and 70 have a temperature of approximately a room temperature (about 25° C.), the shell membrane is rapidly cooled simultaneously after compressing the spherical capsule C1. As a result, the capsule is changed into an aspherical shape which is defined by the dies 68 and 70 and the shell membrane is gelled again.

It is preferred that the time for maintaining the compression of the capsule between the dies 68 and 70 may be a time enough for the capsule to get a desired aspherical shape and to be suppressed from restoring by gelling the shell membrane. The time may be properly determined. The capsule, whose shell material contains gelatin and glycerin, is sufficiently maintained to compress in a time as short as 5 seconds. The time for compressing may be a relatively short time, partly because the heated shell membrane is in a semi-sol state and easily deform into a desired shape by compressing, and partly because the shell membrane having a low water content is low in elasticity and does not yet reach complete sol state, so that it can restore in the gel state rapidly.

Thus, when the capsule in the lower die 70 reaches the end of the forming machine 52, it is formed into the desired aspherical capsule C2. Then, the lower die 70 changes its direction downward along the driving pulley 66, and drops the aspherical capsule C2 down into a collecting box 72 for products.

Thereafter, the aspherical capsule C2 may be again dried if necessary. Because the spherical capsule C1 has been dried to have a low water content in the shell membrane, the second drying of the aspherical capsule C2 brings neither wrinkle nor large deformation on the surface of the shell membrane.

Figure 4:
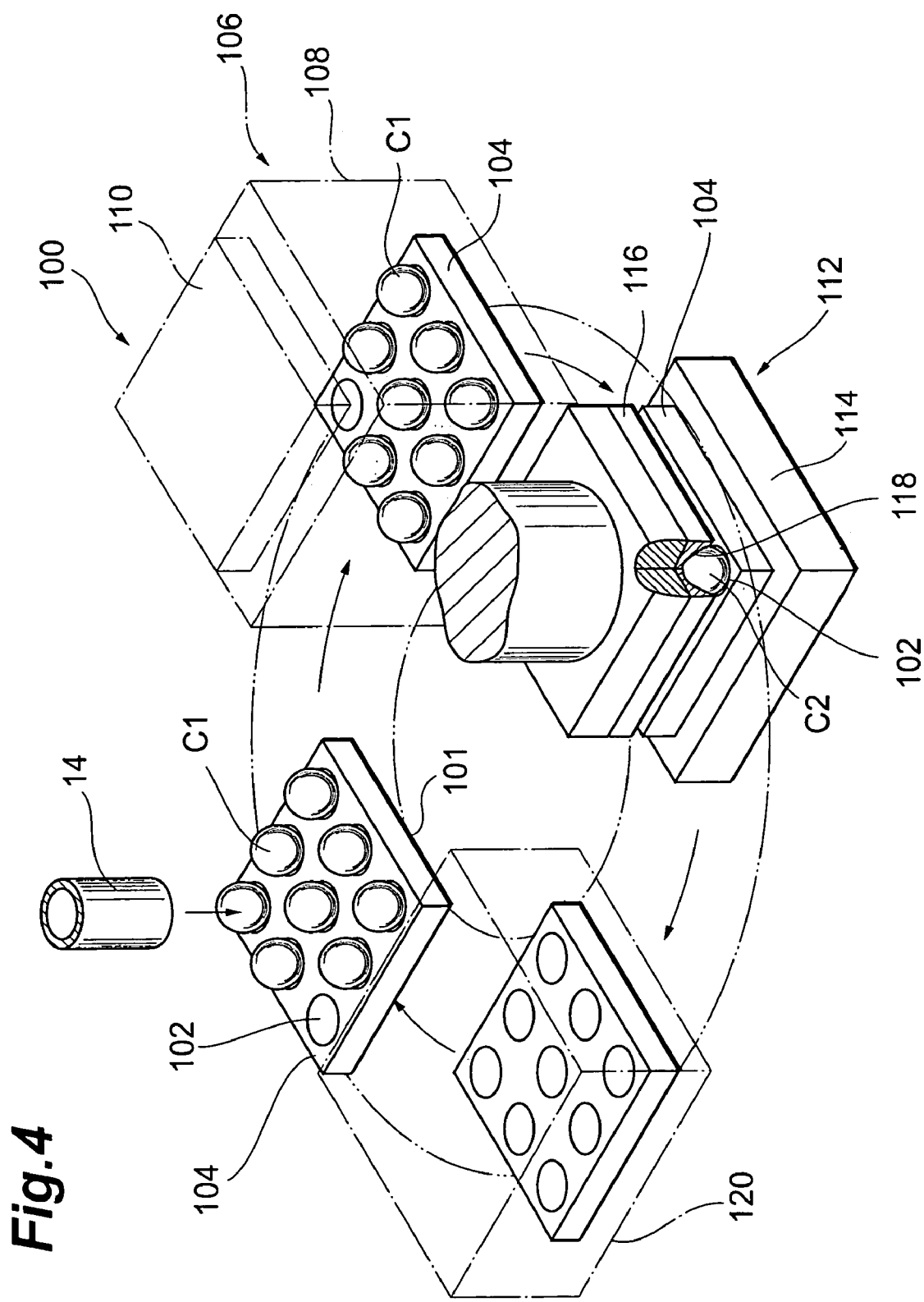
FIG. 4 shows another embodiment of an apparatus for manufacturing an aspherical seamless capsule of the present invention.

FIG. 4 shows another preferable embodiment of the aspherical capsule manufacturing apparatus 16 according to the present invention. Although the aspherical capsule manufacturing apparatus in the above mentioned embodiment can manufacture the aspherical capsules C2 continuously, the capsules C2 may be manufactured in a manner of batch. FIG. 4 shows an example of a batch type aspherical capsule manufacturing apparatus.

The aspherical capsule manufacturing apparatus 100 shown in FIG. 4 comprises a die plate 104 having a plurality of concaves 102 on its surface. The die plate 104 is disposed on a capsule loading part 101 positioned below the storage 14. The dried spherical capsules C1 are loaded one by one from the storage 14 to the associated concaves 102.

The aspherical capsule manufacturing apparatus 100 also comprises a heater 106 for heating a spherical capsule C1 on the die plate 104. In order to heat the surfaces of a plurality of the spherical capsules C1 as evenly as possible, the heater 106 preferably includes a heating chamber 108, and a microwave radiation part 110 that is disposed in the chamber and radiates a microwave. Therefore, the die plate 104 should be made from a material that is resistant to heating by the microwave and resistant to adhesion by the spherical capsule C1. Specifically, the material is preferably a fluorine resin (for example, polytetrafluoroethylene, tetrafluoroethylene-perfluoroalkylvinyl ether copolymer, tetrafluoroethylene-hexafluoropropylene copolymer, tetrafluoroethylene-ethylene copolymer, polychlorotrifluoroethylene, chlorotrifluoroethylene-ethylene copolymer, polyvinylidene fluoride, polyvinyl fluoride). For the batch type heater 106, a contact type such as an ultrasonic type, a radio frequency heating type, a hot air type and a heating layer type using a heat medium, or a non-contact type using an infrared ray may be employed.

Moreover, the aspherical capsule manufacturing apparatus 100 has a forming machine 112 at the back of the heater 106. The forming machine 112 shown in FIG. 4 comprises a vertical compression molding machine which includes a fixed stage 114 and a movable die plate 116 that can vertically move above it. On the lower surface of the movable die plate 116, there are formed concaves 118 that are corresponding to concaves 102 on the die plate 104. The die plate 104 is taken out of the heater 108, and then positioned and fixed on the stage 114. Then, the movable die plate 116 is moved downward from above of the die plate 104.

The aspherical capsule manufacturing apparatus 100 of this embodiment also comprises a washer 120 for washing the die plate 104.

Further, the capsule loading part 101, the heater 108, the forming machine 112 and the washer 120, which are the constituent components of the aspherical capsule manufacturing apparatus 100, are arranged in a circle, as shown in FIG. 4. With this arrangement, when the die plate 104 is circulated along the circular orbital as shown by a double dot-dashed curve in FIG. 4, a plurality of the spherical capsules C1 can be transferred intermittently from the capsule loading part 101, through the heater 108 and the forming machine 112, to the washer 120.

Now, a method for manufacturing the aspherical capsule C2 by using the aspherical capsule manufacturing apparatus 100 as described above will be explained briefly.

First, as explained with reference to FIG. 1, the dried spherical capsules C1 are temporarily stored in the preserver 14. Then, the spherical capsules C1 are fed one by one from the storage 14 to the respective concaves 102 of the die plate 104 placed in the capsule loading part 101. In this method, it is not necessary to load the spherical capsules C1 in the all the concaves 102, as shown.

Next, the die plate 104 is moved into the heater 106, and then irradiated with a microwave from a microwave irradiation part 110 to heat the spherical capsules C1 on the die plate 104. The capsules are heated until the shell membranes change to semi-sol state in the same manner as in the machine 16 shown in FIG. 2.

The spherical capsules C1, whose shell membranes are heated in the heater 106 to get semi-sol state, are transferred to the forming machine 112. After the die plate 104 is set at a given position in the forming machine 112, the movable die plate 116 is lowered from above of the die plate 104. Consequently, the heated spherical capsules C1 on the die plate 104 are compressed between the die plates 104 and 116, so that the aspherical capsules C2 having a desired shape which coincides with the shape defined by the concave 118 on the lower face of the movable die plate 116 and the concave 102 on the upper face of the die plate 104.

In this case, it is preferable that the speed for lowering the movable die plate 116, i.e., the speed for compressing the capsule is a relatively high speed to prevent the shell membrane from restoring to the gel during the compression of the capsule. The fixed stage 114 is preferably provided with a cooling means for a shorter compression retention time if desired, because the lower die plate 104 receives heat from the heated spherical capsule C1 and has a relatively high temperature.

The capsules C2 which are formed in the desired aspherical shape by the forming machine 112 is taken out as products, after the movable die plate 116 is elevated. Then, the emptied die plate 104 is transferred to the washer 120, washed, and returned to the capsule loading part 101 to carry out a following loading process.

Figure 6A:
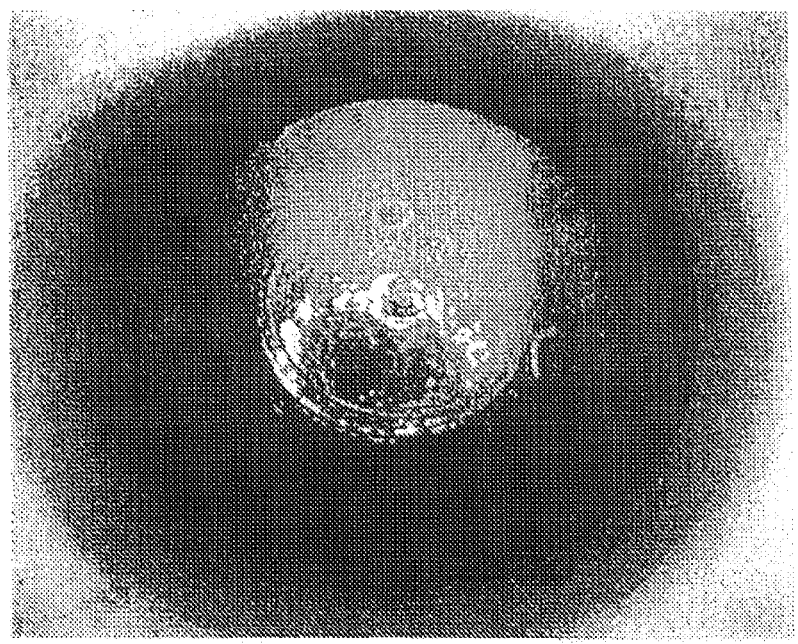
FIG. 6A shows an aspherical seamless capsule obtained by a method of the present invention.
Figure 6B:
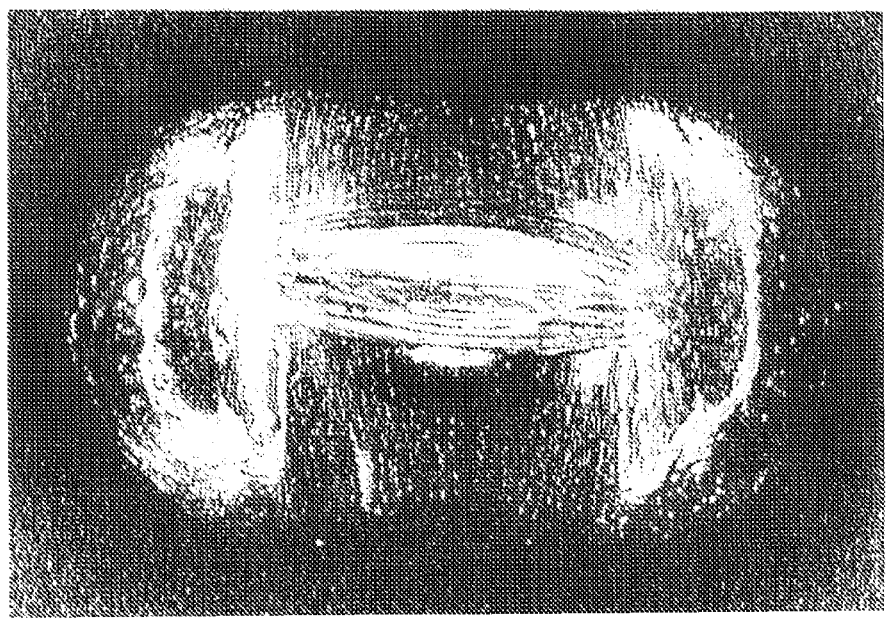
FIG. 6B shows an aspherical seamless capsule obtained by a conventional method.

The resulting aspherical capsule C2 may be again dried if necessary. Because the spherical capsule C1 has been dried to have a low water content in the shell membrane, the second drying of the aspherical capsule C2 brings neither wrinkle nor large deformation on the surface of the shell membrane. It should be noted that FIGS. 6A and 6B show a comparison of capsules provided by a conventional method and one example of the present invention.

The preferable embodiment of the present invention has been described in detail. It will be obvious that the present invention is not limited to the embodiments described above.

For example, although the embodiment shown in FIG. 2 employs a belt type compression molding machine 52, it is also possible to use a roller type machine wherein the spherical capsule is pinched and formed between two rollers having forming surfaces. Also, although the compression molding machine 52 of the belt type described above uses the dies 68 and 70, which face each other to define forming surfaces, the machine 52 may be employed and a die and a punch adapted to be inserted into the die. Moreover, various types of forming machines such as a diaphragm type wherein a spherical capsule is passed through a tube-shaped forming jig having a smaller diameter of the diaphragm than that of the spherical capsule are available.

In the aspherical capsule manufacturing apparatus 16 and 100 shown in FIG. 2 and FIG. 4, the capsule is heated so that the membrane may become to the semi-sol state, before it is compressed. However, the dried spherical capsule C1 may be heated, while compressed, to semi-sol state. In this case, for example, the spherical capsule C1 is placed between the die plates 104 and 116 shown in FIG. 4; a given compression force is imposed between the die plates 104 and 116; and then the compression force is set in such a way that the space between the die plates 104 and 116 may not narrowed with the gelled membrane, but narrowed with the semi-sol membrane. The space can be thus adjusted to control the heating temperature at a relatively moderate accuracy.

EXAMPLES

Next, a method for manufacturing an aspherical capsule of the present invention carried out in practice will be described.

Example 1

In this example, a filler containing a medicine 1 μg, a medium-chain triglyceride 98.70 mg and absolute ethanol 1.30 mg, and a shell material containing gelatin 56.01 mg, glycerin 8.34 mg, caramel 1.95 mg and purified water 84.29 mg were used to prepare a spherical capsule. For the preparation of the spherical capsule, a machine having a construction as shown in FIG. 1 was used. Specifically, Spherex (trademark) made by Freund Corporation was used. The spherical capsules obtained by the spherical capsule manufacturing machine were dried by using a rotational drum type dryer under a condition as follows. Amount of the aspherical capsule treated: 1.4 kg; drum rotation speed: 30 rpm; drying air temperature: 25° C.; drying air humidity: RH45%; amount of the drying air: 1.4 m$^3$/min, and drying time: 20 hours. Each of the spherical capsules taken out of the dryer had a water content of 9% by weight in the shell membrane and a diameter of 6.7 mm.

In this example, the dried spherical capsule C1 thus obtained was formed into an aspherical capsule C2 by using an aspherical capsule manufacturing apparatus 100 equipped with a microwave heater 106 as shown in FIG. 4. The apparatus used in practice was not an automatic type but a manual type, and the compressing machine and the upper die plate were not integral.

First, the capsules C1 were loaded on the lower die plate 104 made of Teflon resin, covered with the upper die plate having the same shape, and then placed in the heater 106. The number of the capsules loaded on the die plate 104 is "53". The concaves 102 and 118 were formed to have a same shape and an opening diameter of 7.7 mm on the upper and lower die plates 104 and 116. The microwave heater 106 was operated at a microwave output of 2 kW and a microwave irradiation time of 40 sec. After heated, the capsules had a surface temperature of about 100° C., and so had a semi-sol shell membranes.

After heated, the capsules were rapidly taken out of the heater while sandwiched between the upper and lower die plates, and then loaded with 200 kgf for 1 minute by a compressing machine to be formed and cooled.

The obtained capsule C2 had a both-side-equally-convex spherical shape in accordance with the shapes of the concaves 102 and 118 of the die plates 104 and 116. 8 samples of the aspherical capsules just after compressed had average sizes of 7.65 mm in longer diameter d1 and 4.85 mm in shorter diameter d2 with a ratio of 1.58 in longer diameter relative to shorter diameter. One of the aspherical capsule obtained is shown in FIG. 6A (Example 1).

Next, one of the aspherical capsules C2 thus obtained was stored at 25° C. The change of its shape with time is as shown in the following table.

TABLE 1

| sizes | Just after forming | one day later | 3 days later | 5 days later | 7 days later |
|---|---|---|---|---|---|
| Longer diameter d1 (mm) | 7.60 | 7.62 | 7.60 | 7.59 | 7.60 |
| Shorter diameter d2 (mm) | 4.85 | 4.93 | 4.93 | 4.91 | 4.94 |
| Ratio (d1/d2) | 1.57 | 1.55 | 1.54 | 1.55 | 1.54 |

From this table, it can be understood that no change in shape of the aspherical capsule (restoration to the spherical shape) occurred.

Example 2

Figure 5:
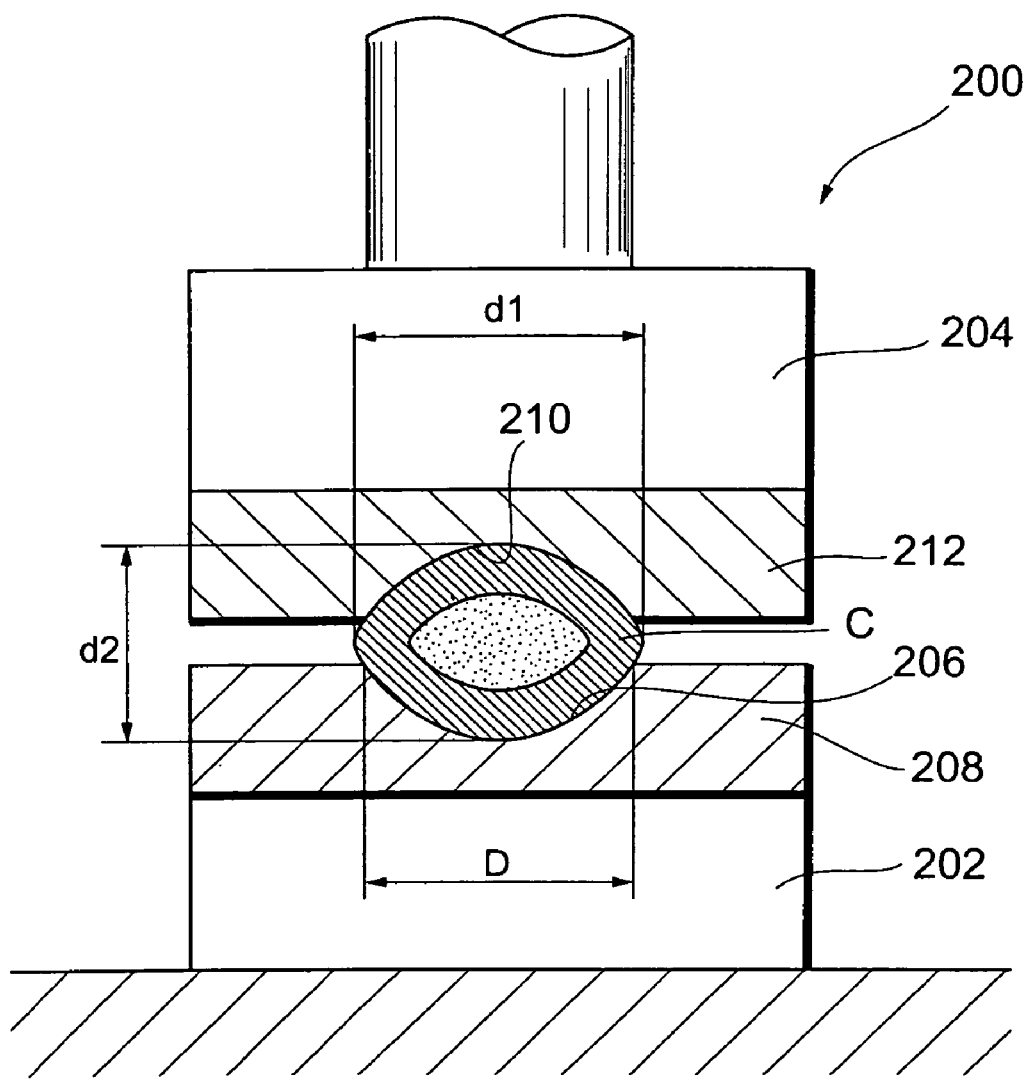
FIG. 5 shows a compression test machine which was used as a forming machine in Example.

In Example 2, the same dried spherical capsule C1 as in Example 1 was formed into an aspherical capsule by using the biaxial roller heater in the aspherical capsule manufacturing apparatus shown in FIG. 2 and a compression test machine 200 as shown in FIG. 5.

First, the biaxial roller heater was set to have a surface temperature of 115° C., a roller rotation of 25 rpm and a heating time (a time for the dried spherical capsule to be placed between the rollers until discharged) of 2 minutes. After discharged, the capsule had a surface temperature of about 100° C., and so had a semi-sol shell membrane.

The compression test machine 200 comprises a fixed stage 202 and a movable unit 204 disposed above the stage 202. A die plate 208 is fixed on the fixed stage 202 and has one concave 206 at the center of its upper surface. A die plate 212 is fixed on the lower face of the movable unit 204 and has one concave 210 at the center of its lower surface. The concaves 206 and 210 of the die plates 208 and 212 have the same shape, and each of their bottom surfaces are shaped as a part of the spherical face of a sphere having a radius of 6 mm. An opening diameter D of each of the concaves is 7.5 mm. The both die plates 208 and 212 were kept to have a temperature of 25° C.

The spherical capsule just after discharged from the heater was placed in the concave 206 on the lower die plate 208 of the compression test machine 200, and then compressed between the die plates 208 and 212 by lowering the movable unit 204 at a compression speed of 300 mm/min. When the movable unit 204 reached the lowest level thereof (the level shown in FIG. 5), the machine was set to form a 1 mm distance between the die plates 208 and 212. A compression retention time (i.e., a time for the movable unit 204 which reached the lowest level to be kept until lifted) was set to be 5 seconds. The capsule C2 thus obtained after the compressing process had approximately a both-side-equally-convex-spherical shape in accordance with the concaves 206 and 210 on the die plates 208 and 212. 5 samples of the aspherical capsules just after compressed had average sizes of 8.22 mm in longer diameter d1 and 5.43 mm in shorter diameter d2 with a ratio of 1.51 in longer diameter relative to shorter diameter. The resulting aspherical capsule C2 was different in size from that in Example 1, because the concaves 102 and 118 of the die plates 104 and 116 were different in shape from the concaves 206 and 210 of the die plates 208 and 212.

Thereafter, the aspherical capsule C2 thus obtained was stored at 40° C. The change of its shape with time is shown in the following table.

TABLE 2

| sizes | just after forming | one day later | 3 days later | 5 days later | 7 days later |
|---|---|---|---|---|---|
| longer diameter d1 (mm) | 8.22 | 8.04 | 7.78 | 7.86 | 7.90 |
| shorter diameter d2 (mm) | 5.43 | 5.57 | 5.59 | 5.60 | 5.57 |
| ratio (d1/d2) | 1.51 | 1.44 | 1.39 | 1.40 | 1.42 |

From this table, it can be understood that a slight change in shape after 1 day of storage, i.e., a slight restoration to a sphere shape could be observed as in Example 1, but that almost no change in shape was recognizable afterward. The surface had the same shape as that shown in FIG. 6A.

Comparative Example

An aspherical capsule was formed in the almost same way as in Example 1, except that no caramel was used, and according to a method described in JP Application Laid-Open No. 2000-325431. One example of the aspherical capsule obtained is shown in FIG. 6B (comparative example). It can be understood that the capsule had wrinkles on the shell membrane surface because it was dried to shrink. The capsules obtained also varied in shape.

INDUSTRIAL APPLICABILITY

As described above, the present invention allows manufacturing an aspherical capsule for a shorter forming time and at a better production efficiency, because a spherical capsule whose shell membrane is dried to semi-sol state is formed into the aspherical capsule. The present invention also can suppress the shell membrane from restoration.

Also, an aspherical capsule, which is manufactured from a dried spherical capsule, does not need being dried after it is formed. It can be dried, if needed, with a very small amount of a solvent to remove. Therefore, a product thus obtained has no wrinkle and does not vary in shape.

Moreover, the present invention uses a dried spherical capsule, and hence allows easiness in treatment such as storage and transportation and improves a production efficiency. In other words, the present invention provides an effect that a production plan is freely designed because a dried spherical capsule can be stored and formed into an aspherical capsule at any desired time.

As described above, the present invention can be used widely in a production industry such as pharmaceutical, confectionery, food and the like.

The invention claimed is:

1. A method for manufacturing an aspherical seamless capsule comprising:
   a first step for providing a seamless capsule having a filler encapsulated with a shell membrane;
   a second step for drying said seamless capsule provided in said first step until a predetermined percentage content of solvent in said shell membrane reaches a predetermined value;
   a third step for heating said seamless capsule obtained in said second step so that said shell material may get to a semi-sol state; and
   a fourth step for forming said seamless capsule obtained in said third step into a predetermined aspherical shape in a compression molding process using dies.

2. A method for manufacturing an aspherical seamless capsule according to claim 1, wherein said shell membrane is a material containing water as a solvent, and said shell membrane of said seamless capsule obtained in said second step has a solvent content of 20% by weight or less.

3. A method for manufacturing an aspherical seamless capsule according to claim 1 or 2, wherein the heating in said third step uses microwave.

4. A method for manufacturing an aspherical seamless capsule according to claim 1 or 2, wherein said forming in said fourth step is carried out while cooling said seamless capsule.

5. An apparatus for manufacturing an aspherical seamless capsule comprising:
   a heating part for heating a spherical seamless capsule having a filler encapsulated with a shell membrane; and
   a compression molding machine that uses dies for forming said seamless capsule into an aspherical shape, while said shell membrane of said seamless capsule heated by said heating part is in a semi-sol state.

6. An apparatus for manufacturing an aspherical seamless capsule according to claim 5, wherein said heating part is a heater using microwave.

* * * * *